United States Patent [19]
Rainin

[11] 4,403,354
[45] Sep. 13, 1983

[54] INTRAOCULAR LENS HAVING A FIXATION MECHANISM

[76] Inventor: Edgar A. Rainin, 2260 Gladstone Dr. #3, Pittsburgh, Calif. 94565

[21] Appl. No.: 306,420

[22] Filed: Sep. 28, 1981

Related U.S. Application Data

[63] Continuation of Ser. No. 54,953, Jul. 5, 1979, abandoned.

[51] Int. Cl.³ .......................... A61F 1/16; A61F 1/24
[52] U.S. Cl. .................................................. 3/13
[58] Field of Search .............................................. 3/13

[56] References Cited
U.S. PATENT DOCUMENTS 3,906,551 9/1975 Otter ........................................... 3/13
4,134,161 1/1979 Bayers ......................................... 3/13

Primary Examiner—Clifford D. Crowder

[57] ABSTRACT

An intraocular lens having a fixation mechanism which includes a lens or optical portion having a resilient appendage attached at one end to the optical portion. The other end of the resilient appendage slidably engages the lens forming a closed loop which adjustably extends from the lens portion.

13 Claims, 8 Drawing Figures

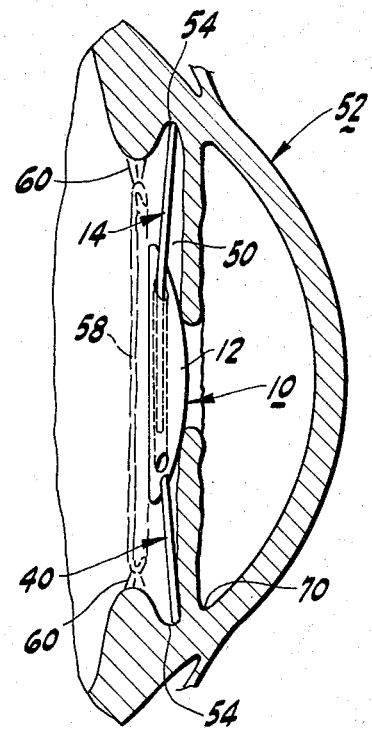

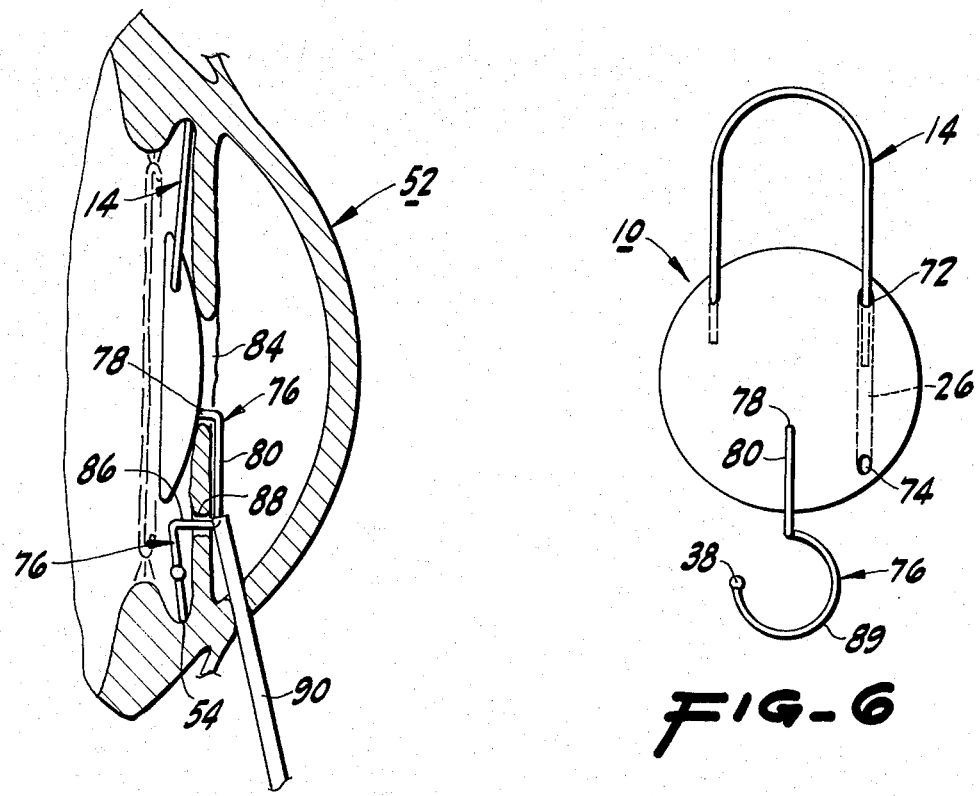
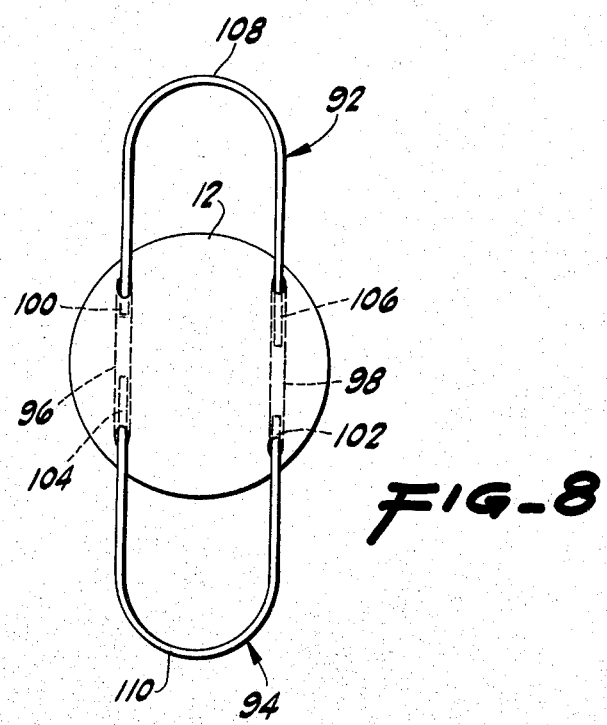

INTRAOCULAR LENS HAVING A FIXATION MECHANISM

This is a continuation, of application Ser. No. 054,953 filed July 5, 1979, now abandoned.

BACKGROUND OF THE INVENTION

The present invention relates to an intraocular lens or pseudophakos which is intended for placement in either the anterior or posterior chamber of an eye after removal of the natural lens of an eye as the result of a cataract condition or other like conditions which destroy the functioning of the natural lens.

Intraocular lenses have been used increasingly in recent times since the use of intraocular lenses provides the cataract patient with remarkable visual acuity. In general intraocular lenses have produced excellent results. Problems still remain in placement of the pseudophakos without inflicting damage to the eye as well as insuring continual fixation of the intraocular lens during the years following cataract surgery. There are several examples of intraocular lenses which fix to the iris. Most notably are the U.S. Pat. No. 3,906,551 issued to Otter and U.S. Pat. No. 4,085,467 issued to Rainin et al. The original intraocular lens development by Strampelli and Barraquer simply wedged the intraocular lens between opposite sides of the anterior chamber of the eye immediately above the iris. The early models occasionally achieved a success but were not acceptable because of fixation problems resulting from improper sizing of the lens structure, and damage to the eye during and after insertion of the lens, as a result of endothelial touch. The original Barraquer lens has been recently revived and achieved greater success by the addition of springy appendages which alleviates necessity of exactly sizing the lens and insertion of a Barraquer type lens in the posterior chamber of the eye. The modern version of the Barraquer lens is known as the Shearing lens which includes a pair of hook-shaped legs which attach to the lens at points generally opposite one another. Surgeons have found acceptable fixation in the posterior chamber in an annular notch known as the ciliary sulcus.

A Shearing lens has several disadvantages in that it may be used with extra capsular surgery only. The Shearing lens is inserted in the posterior chamber by first inserting one appendage through the pupil to the ciliary sulcus, coiling the second appendage, and releasing the same after the lens portion and the secondary appendage has passed through the pupil to the posterior chamber to also obtain fixation at the ciliary sulcus. It has been found that the free end of the springy appendage of the Shearing lens catches eye structures during insertion and centering which adds greatly to the difficulty of insertion. Further, a dilated pupil, which may occur spontaneously or may be medically induced post-operatively, permits the inner edge of the iris to travel under the lens since a single appendage permits bowing. In addition, problems of centering the intraocular lens beneath the pupil occur since the hook-like appendage often catches on the iris, lens capsule, and other portions of the eye. Moreover, other problems associated with twisting about the single appendage, eg: the optical defect of induced cylinder, also occur.

All in all there is a need for a wedging type lens which may be easily placed in the posterior or anterior chamber of the eye which possesses great stability and minimizes damage to the eye during and after insertion.

SUMMARY OF THE INVENTION

In accordance with the present invention a novel intraocular lens structure is provided.

The intraocular lens structure includes a lens or optical zone portion which is intended for placement against the side of the iris and functions as a optical replacement for the removed natural lens of the eye. The lens includes a resilient appendage attached at one end thereof to the lens. The other end of the appendage is turned back toward the lens and slidably engages the same. Thus, a loop is formed having an end point which possesses the characteristic of having an adjustable distance in relation to the lens portion. Such means for slidably engaging the other end of the resilient appendage may take the form of providing an opening in the lens portion for insertion of the other end of the resilient appendage. In this manner, the end of this resilient appendage slightly engages the side portions of the opening. Thus, the opening serves as a guide for the other end of the resilient appendage.

In addition, the intraocular lens of the present invention may include a second appendage which is also attached to the lens portion. It should be noted that any of the appendages may attach to the lens or a haptic surrounding the lens portion. In this regard, the haptic may have a plurality of protuberances which are adapted for contacting the periphery of the iris eg: the angle in the anterior chamber of the eye or the ciliary sulcus in the posterior chamber of the eye. The second appendage may also be a resilient appendage having one end attached to the lens and including means for slidably engaging the other end of the second appendage to the lens portion. Again, the means for engaging the other end of the second resilient appendage may also take the form of an opening in the lens portion for guiding engagement of the other end of the second appendage.

The invention of the present application may also embrace an embodiment where the opening in the lens portion passes completely through the lens to form a tunnel having first and second entrances thereto. The appendage attached to the lens portion would pass through the tunnel such that a first portion of the appendage would lie outside the lens between the attachment of one end of the appendage to the lens and the first entrance to the tunnel. Also, an intermediate portion of the appendage would position within the tunnel and a third portion would extend outside the second entrance to the tunnel. A further variation would encompass forming a second opening in the lens to slidably engage the other end of the appendage or to guide relative movement between the other end of the appendage and the lens portion.

The invention may take another embodiment where the second appendage is a resilient appendage having a point of attachment to the lens portion at one end thereof and including means for slidably engaging the other end of the second appendage or guiding movement of the other end of the second appendage in relation to the lens portion. In this regard the means for slidably engaging the other end of the first and second appendages may comprise a pair of openings each sized for insertion of one of the first and second resilient appendages. The first and second resilient appendages in this case may also have the first ends attached within one of the pair of openings. This embodiment would reduce the amount of labor required to produce a usable lens.

In essence, the lens of the present invention includes a lens portion having an appendage attached thereto in one end thereof, and means for guiding movement of the appendage relative to the lens portion.

It may be apparent that a novel and useful intraocular lens having an improved fixation mechanism has been described.

It is therefore an object of the present invention to provide an intraocular lens having a fixation mechanism which may be placed in either the anterior or posterior chamber of the lens for correction of aphakia which minimizes damage to the eye during and after insertion.

It is another object of the present invention to provide an intraocular lens having a fixation mechanism which minimized dislocation during dilation of the pupil of the eye during and after insertion of the intraocular lens within the eye.

It is yet another object of the present invention to provide an intraocular lens having a fixation mechanism which facilitates centering of the intraocular lens during the insertion process.

It is still another object of the present invention to provide an intraocular lens having a fixation mechanism which resists twisting along the axis of fixation thus preventing optical distortions within the eye such as induced cylinder.

It is another object of the present invention to provide an intraocular lens having a fixation mechanism which exhibits adjustability and stability after placement within the eye.

It is another object of the present invention to provide an intraocular lens having a fixation mechanism which is easily manufactured.

The invention possesses other objects and advantages especially as concerns particular characteristics and features thereof, which will become apparent as the specification continues.

BRIEF DESCRIPTION OF THE DRAWINGS

FIG. 1 is a top plan view of an embodiment of the invention, depicting adjustable appendages in phantom.

FIG. 2 is a sectional view of a human eye showing the embodiment of the invention in FIG. 1 placed within the posterior chamber of the eye.

FIG. 3 is a top plan view of another embodiment of the present invention.

FIG. 4 is a top plan view of another embodiment of the present invention.

FIG. 5 is a top plan view of another embodiment of the present invention.

FIG. 6 is another embodiment of the present invention.

FIG. 7 is a sectional view of a human eye showing the embodiment of FIG. 6 placed in the posterior chamber of the eye.

FIG. 8 is a top plan view of another embodiment of the present invention.

For a better understanding of the invention, reference is made to the following detailed description.

DESCRIPTION OF THE PREFERRED EMBODIMENTS

Various aspects of the present invention will evolve from the following detailed description of the preferred embodiments thereof which should be taken in conjunction with the heretofore described drawings.

The invention as a whole is shown in the drawings by reference character 10 and includes as one of its elements an optical lens portion or optical zone 12 may be formed from methylmethacrylate, quartz, opthalmic glass, and other materials known in the art. Of course, lens portion 12 must be biologically inert and transparent such that optical correction may inure. A first appendage 14 includes a first end 16 which is attached to lens portion 12 by gluing, sonic welding, and like processes known in the art. The first appendage 14 may be integrally molded with lens portion 12. Appendage 14 also includes a second end 18 and an intermediate portion 20 between ends 16 and 18, which contacts the periphery of the iris. The invention also includes as one of its elements means 22 for guiding movement of end 18 in relation to lens portion 12. Means 22 may take the form of means 24 for slidably engaging end 18 to lens portion 12. The embodiment shown in FIG. 1 externalizes means 22 and 24 in the form of an opening 26 in lens portion 12 sized for insertion of end 18 of appendage 14 therewithin. Any force on intermediate portion 20 of appendage 14 would cause end 18 to slide further into opening 26. Intermediate portion 20 would move toward lens portion 12 a distance shown by arrows 28, FIG. 1.

Turning to FIGS. 3 and 4 it may be seen that other embodiments of the invention are shown. In FIG. 3, appendage 14a is attached to lens portion 12 at end 16A by the same methods described under appendage 14A above. Means 22 may take the form of an opening 30 which passes or tunnels through lens portion 12. The end 32 of appendage 14A fits within another opening 34 which may or may not pass through lens portion 12. As shown in FIG. 3, opening 34 does pass through lens portion 12 because of manufacturing expedient. Turning to FIG. 4, it may be seen that appendage 14B attaches to lens portion 12 at end 16B. Opening 30 guides the remaining portion of appendage 14B in relation to lens portion 12. However, the end 36 of appendage 14B is free having a cap 38 for the purpose of preventing punctures within the eye structure.

Returning to FIG. 1 it may be seen that the embodiment depicted therein includes a second appendage 40 which fixes to lens portion 12 at its end 42. Second appendage 40 has means 44 for guiding movement of the remaining portion 46 of appendage 40, including end 48. As may be seen appendages 14, 14A, 14B, and 40 may be resilient which permits flexure of the above identified appendages upon the application of pressure between the ends thereof.

In this regard, attention is drawn to FIG. 2 which depicts intraocular lens 10 placed within the posterior chamber 50 of human eye 52. As may be seen from FIG. 2, the first appendage 14 and second appendage 40 bear in the annular notch known as the ciliary sulcus 54. Means 22 and 44 for guiding the remaining portion of appendages 14 and 40 (apart from fixed ends 16 and 42 respectively) permit the appendages 14 and 40 to shorten the distance indicated by arrows 28 and 56, FIG. 1. In the case where appendages 14 and 40 are resilient such shortening will result in the application of pressure by the appendages on ciliary sulcus 54 which tends to hold intraocular lens 10 in place. FIG. 2 depicts an extra capsular cataract removal where the shell of the natural lens 58 remains attached to the zonules 60. Since appendages 14 and 40 form a closed loop many of the disadvantages of the open loop appendage system have been eliminated yet the adjustability afforded the former open loop system has been retained.

Turning to FIG. 5, another embodiment of the present invention is shown wherein an appendage 14C forms a closed loop in relation to lens 12. Appendage 14C has one end 16C attached to lens portion 12. Means 22 takes the form of an opening 62 which may pass through lens portion 12, haptic 64, or both. As shown in FIG. 5, opening 62 extends through lens portion 12. Opening 62 may be constructed to extend only partially through lens portion 12. Haptic 64 includes a pair of protuberances 66 and 68 which are intended for contact with ciliary sulcus 54 or angle 70 (anterior chamber placement), FIG. 1. This embodiment would provide three point fixation within the posterior or anterior chamber of eye 52; contact being made by protuberances 66 and 68 and a rounded portion 72 of looped appendage 14c. Of course, appendage 14C is extendable and retractable in the same manner as loop 14 of FIG. 1.

The embodiment of FIG. 6 depicts appendage 14 as essentially identical to the embodiment depicted in FIG. 1. Opening 26 includes a first entrance 72 and a second entrance 74. Appendage 76 attaches to lens 12 at end 78. Appendage 76 includes a first portion 80 which extends through pupil 84 of eye 52, FIG. 7. Second portion 86 of appendage 76 is adapted for passing through an iris opening 88 which may be provided during cataract surgery. Enlarged end portion 89 extends to the periphery of the iris for engagement therewith, eg: ciliary sulcus 54. A cap 38 blunts the end of appendage 76 to prevent damage to the internal structure of the eye during and after insertion of second appendage 76. Surgical tweezers 90 may be used to stabilize intraocular lens 10 during insertion, FIG. 7.

With reference to FIG. 8 another embodiment of the invention is illustrated where a first appendage 92 and second appendage 94 both includes means 22 for guiding the appendages in any movement relative to lens portion 12. Means 22 takes the form of a pair of openings 96 and 98 which pass through lens portion 12. The first ends 100 and 102 of appendages 92 and 94 respectively fix within openings 96 and 98 by known methods such as sonic welding, fusion, and the like. The second ends 104 and 106 slidingly engage the side portions of openings 96 and 98. Thus, the bent portions 108 and 110 of appendages 92 and 94 lie at an adjustable distance from lens portion 12. Where appendages 92 and 94 are resilient any pressure on the same will result in a spring action which tends to force appendages 92 and 94 into their original position as depicted on FIG. 8.

It may be apparent that all of the embodiments described hereinabove include an appendage 14 extending from lens portion 12 which forms a closed loop in relation to the lens portion, means 22 for guiding the movement of the appendage 14 in relation to the lens portion 12, and means 112 (FIG. 1) for urging appendage 14 away from lens portion 12. Means 112 may simply take the form of providing appendage 14 with resilience or springiness such that any pressure on appendage 14 toward lens portion 12 will result in means 112 coming into play.

In operation, the user inserts intraocular lens 10 into the anterior or posterior chamber of the eye 52 employing angle 70 or ciliary sulcus 54 at the periphery of the iris to obtain a confining surface for first appendage 14A or 14B or first appendage 14, 14C or 92 in combination with second appendages 40, 76, 96 or haptic 64.

While in the foregoing specification embodiments of the invention have been set forth in considerable detail for the purposes of making a complete disclosure of the invention, it will be apparent to those of ordinary skill in the art that numerous changes may be made in such details without departing from the spirit and principles of the invention.

What is claimed is:

1. An intraocular lens having a fixation mechanism comprising:
   a. a lens portion;
   b. a flexible appendage having one end portion, another end portion, and an intermediate portion between said one and another end portions, said flexible appendage being fixed to said lens portion at said one end portion; and
   c. means for slidably engaging the other end portion of said flexible appendage to said lens portion, said intermediate appendage portion between said one end portion and said another end portion adapted to extend to the periphery of the iris.

2. The intraocular lens of claim 1 in which said means for slidably engaging the other end of said flexible appendage comprises providing an opening in said lens portion for insertion of said other end of said flexible appendage.

3. The intraocular lens of claim 2 in which said flexible appendage is a first appendage and wherein there is provided a second appendage.

4. The intraocular lens of claim 3 in which said second appendage is a flexible appendage.

5. The intraocular lens of claim 4 in which said second appendages attaches to said lens portion at one end thereof and wherein there is provided means for slidably engaging the other end of said second appendage to said lens portion.

6. The intraocular lens of claim 5 in which said means for slidably engaging the other end of said second flexible appendage includes another opening in said lens portion, for insertion of said second flexible appendage.

7. The intraocular lens of claim 3 in which said second appendage has a first portion extending from said lens portion, a second portion intended for passing through the iris opening and an enlarged end portion intended for extending to the periphery of the iris for engagement therewith.

8. The intraocular lens of claim 2 in which said lens portion includes a haptic having a plurality of protuberances adapted for contacting the periphery of the iris.

9. The intraocular lens of claim 2 in which said opening in said lens portion passes therethrough to form first and second entrances to said opening through said lens portion, said flexible appendage passing through said opening through said lens portion such that a first part of said flexible appendage lies between said one end portion of said flexible appendage attached to said lens portion and said first entrance to said opening through said lens portion, a second part of said appendage lies within said opening through said lens portion, and a third part of said appendage extends outside said second entrance to said opening through said lens portion.

10. The intraocular lens of claim 9 in which said opening through said lens portion is a first opening and wherein said lens comprises a second opening which slidably engages said other end portion of said flexible appendage.

11. An intraocular lens having a fixation mechanism comprising:

a. a lens portion;

b. an appendage having at least one end portion fixed to said lens portion and having at least another portion connected to said at least one end portion; and c. means for guiding movement of said another portion of said appendage relative to said lens portion, said another portion of said appendage adapted to contact a portion of the eye.

12. The intraocular lens of claim 11 in which said appendage is a first appendage and wherein there is further provided a second appendage having a first portion extending from said lens portion, a second portion intended for passing through an iris opening and an enlarged end portion intended for extending to the periphery of the iris for engagement therewith.

13. A fixation mechanism for an intraocular lens having a lens portion comprising:

a. an appendage extending from said lens portion and being fixed to said lens portion, said appendage also forming a closed loop in relation to said lens portion and adapted to contact a portion of the eye, said appendage further including means for urging said appendage away from said lens portion;

b. means for guiding movement of a portion of said appendage in relation to said lens portion.

* * * * *